United States Patent
Hunter et al.

(10) Patent No.: US 6,726,725 B2
(45) Date of Patent: Apr. 27, 2004

(54) PROSTHETIC DEVICES EMPLOYING CONTACTING OXIDIZED ZIRCONIUM SURFACES

(75) Inventors: Gordon Hunter, Germantown, TN (US); Ajit Mishra, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/912,626

(22) Filed: Jul. 24, 2001

(65) Prior Publication Data

US 2003/0033020 A1 Feb. 13, 2003

Related U.S. Application Data

(60) Provisional application No. 60/295,272, filed on Jun. 1, 2001.

(51) Int. Cl.[7] ................................................. A61F 2/28
(52) U.S. Cl. ............................... 623/23.54; 623/22.15; 623/23.5; 623/23.55
(58) Field of Search ........................... 623/20.14, 20.32, 623/20.33, 20.34, 20.35, 20.36, 22.11, 22.15, 23.54, 23.55, 23.52, 23.5, 23.15, 22.4, 18.11

(56) References Cited

U.S. PATENT DOCUMENTS

| 5,258,022 A | 11/1993 | Davidson |
| 6,387,132 B1 | 5/2002 | Deppisch et al. |
| 6,447,550 B1 * | 9/2002 | Hunter et al. |

FOREIGN PATENT DOCUMENTS

| WO | WO 98/42390 | 10/1998 |
| WO | WO 99/27871 | 6/1999 |

OTHER PUBLICATIONS

Willmann, G., et al.; Biomaterials, 1996, vol. 17, No. 22, pp. 2157–2162.

* cited by examiner

Primary Examiner—Nicholas D. Lucchesi
Assistant Examiner—Lalita M Hamilton
(74) Attorney, Agent, or Firm—Fulbright & Jaworski L.L.P.

(57) ABSTRACT

Orthopedic implants comprising components of zirconium or zirconium-based alloys having surfaces coated with oxidized zirconium contacting other surface-coated oxidized zirconium are disclosed. Such implants provide low friction, highly wear resistant coatings especially useful in artificial joints, such as hip joints, knee joints, elbows, etc., but also useful in non-articulating implant devices such as bone plates, bone screws, etc.

28 Claims, 1 Drawing Sheet

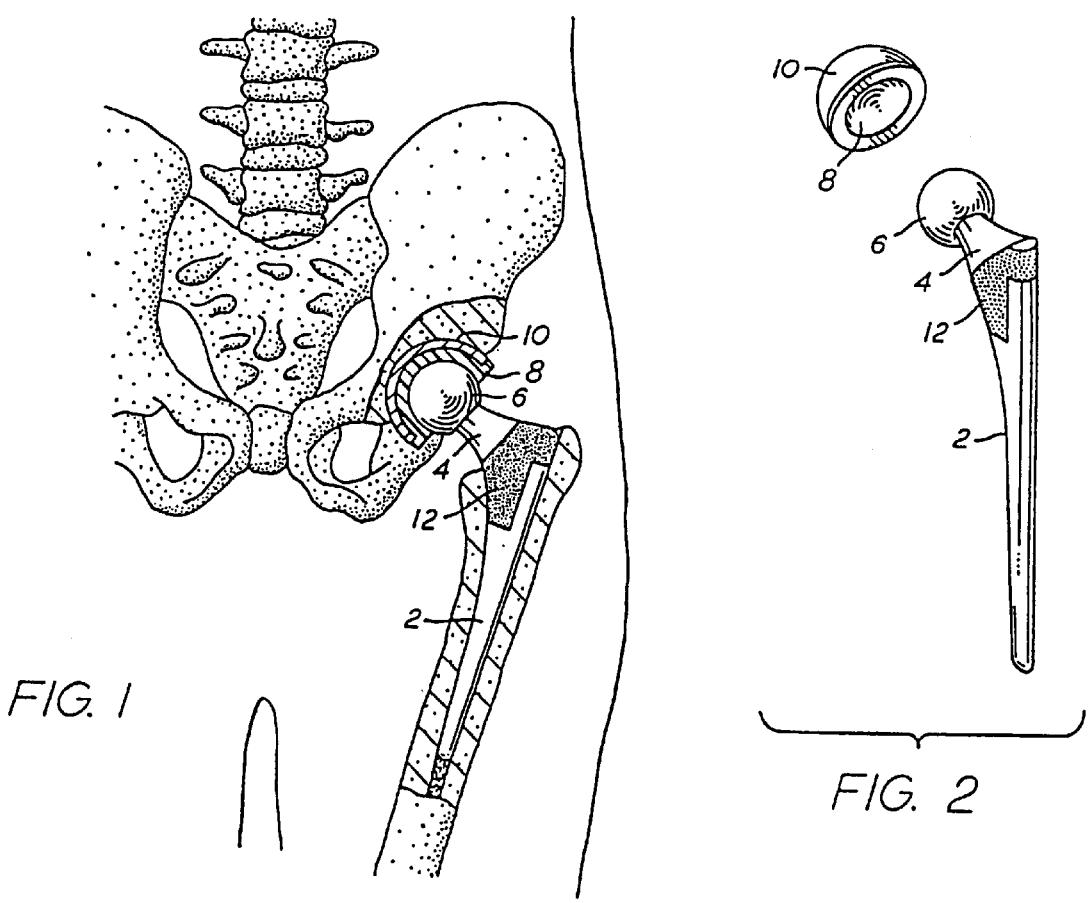
FIG. 1
FIG. 2
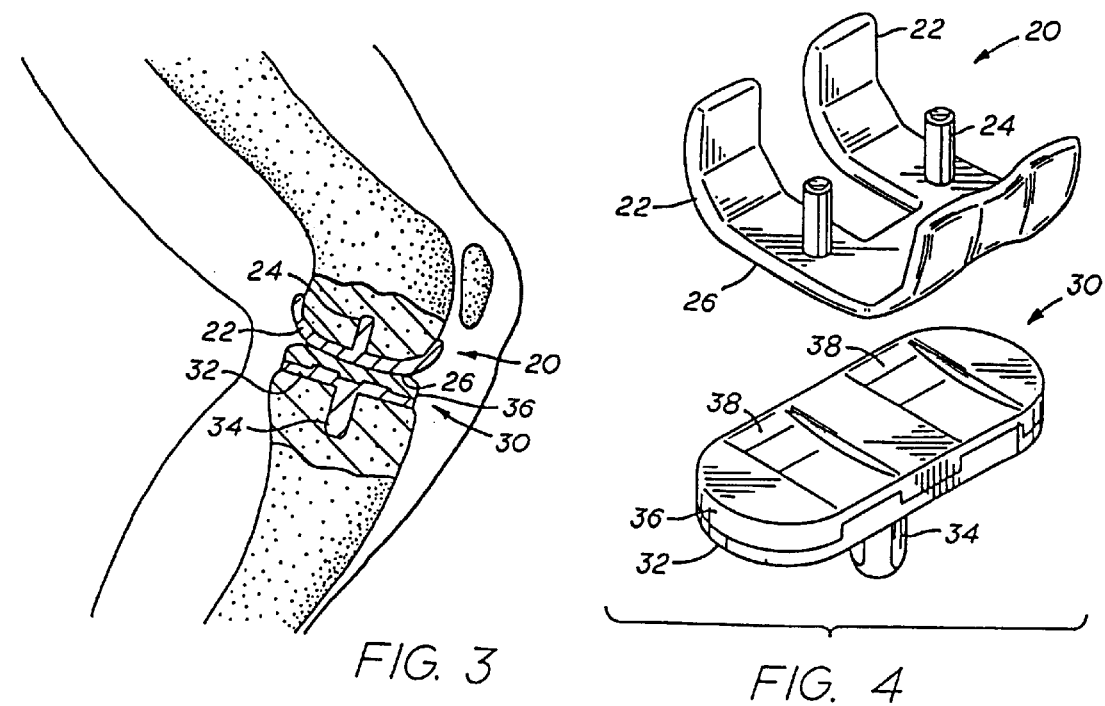
FIG. 3
FIG. 4

PROSTHETIC DEVICES EMPLOYING CONTACTING OXIDIZED ZIRCONIUM SURFACES

This application claims priority to U.S. Provisional Application Ser. No. 60/295,272, filed Jun. 1, 2001.

BACKGROUND OF THE INVENTION

This invention relates to metallic orthopedic implants with load bearing surfaces coated with a thin, dense, low friction, highly wear-resistant coating of oxidized zirconium. The devices of the present invention possess two or more of oxidized zirconium surfaces in which the oxidized zirconium surfaces contact one another in an articulating (i.e., load bearing) or non-articulating (non-load-bearing) manner. Because these high hardness coatings are resistant to galling and fretting, they are particularly useful on the articulating portions of these prostheses. Typically, such prostheses with articulating surfaces were constructed of materials of different hardness. By having one "yielding" surface, such prior art devices eventually form an optimal fit, i.e., a tight tolerance, whereby galling, fretting, and other erosive phenomena are minimized, resulting in longer-lasting prosthetic devices. An example of these early-generation devices is the femoral head of a hip-stem prosthesis which engages a counter-bearing surface in an acetabular cup which is often made of a softer material such as ultra-high molecular weight polyethylene. However, use of contacting surfaces of varying hardness has disadvantages avoided by the unique properties of the present invention. The softer surface is, by nature sacrificial; it will eventually fail, the trade-off being realized in an overall increase in the useful life of the prostheses. Additionally, fretting of the softer surface results in debris that may have deleterious effects on health on the patient. The invention described herein is a particular type of ceramic-on-ceramic prosthesis; its unique compositional properties affords the traditional advantages of ceramic-on ceramic systems while avoiding their major disadvantage.

While efforts have been made to fabricate prosthetic devices having contacting surfaces of the same material, these efforts have had limited success in overcoming the deficiencies of the prior art. By taking advantage of the unique nature of the blue-black or black oxidized zirconium, the instant invention teaches a prosthetic device having contacting surfaces (either articulating or non-articulating) of the same material that dispenses with the need for a yielding or sacrificial surface, yet keeps wear to a minimum. The basic technology upon which the improvement described herein is based, is described in U.S. Pat. No. 5,037,438 to Davidson and pending application 09/381,217, filed Nov. 24, 1999 of Hunter, et al., both of which are fully incorporated by reference herein.

The invention also relates to medical implants having contacting oxidized zirconium surfaces and also having oxidized zirconium coatings on the non-articulating surfaces of an orthopedic implant where the latter oxidized zirconium surfaces provides a barrier between the metallic prosthesis and body tissue thereby preventing the release of metal ions and corrosion of the implant. Additionally, this oxidation process and the associated increase in surface oxygen content and hardness increases the strength of the metal substrate and improves the fatigue properties of the implant.

The longevity of medical implant devices is of prime importance as it is desirable that the implant should function for the complete lifetime of a patient. This is particularly true if the patient is young and the number of surgical revisions is to be kept to a minimum and preferably zero. To this end, orthopedic implant materials should preferably combine high strength, corrosion resistance and tissue compatibility. One of the variables affecting the longevity of load-bearing implants such as hip-joint implants is the rate of wear of the articulating surfaces and long-term effects of metal ion release. A typical hip-joint prosthesis includes a stem, a femoral head and an acetabular cup against which the femoral head articulates. Wear of either or both of the articulating surfaces results in an increasing level of wear particulates and "play" between the femoral head and the cup against which it articulates. Wear debris can contribute to adverse tissue reaction leading to bone resorption, and ultimately the joint must be replaced.

The rate of wear of the acetabular cup and the femoral head surfaces of artificial hips is dependent upon a number of factors which include the relative hardness and surface finish of the materials which constitute the femoral head and the acetabular cup, the frictional coefficient between the materials of the cup and head, the load applied and the stresses generated at the articulating surfaces. The most common material combinations currently used in the fabrication of hip-joint implants include femoral heads of cobalt, titanium, or zirconium alloys articulating against acetabular cups lined with organic polymers or composites of such polymers including, for instance, ultra-high molecular weight polyethylene (UHMWPE) and femoral heads of polished alumina in combination with acetabular cups lined with an organic polymer or composite or made of polished alumina.

Of the factors which influence the rate of wear of conventional hip-joint implants, the most significant are patient weight and activity level. Additionally, heat generated by friction in the normal use of the implant has been shown to cause accelerated creep and wear of the polyethylene cup. Furthermore, there is a correlation between the frictional moment which transfers torque loading to the cup and the frictional coefficient between the femoral head and the surface of the acetabular cup against which the head articulates. Cup torque has been associated with cup loosening. Thus, in general, the higher the coefficient of friction for a given load, the higher the level of torque generated. Ceramic bearing surfaces have been shown to produce significantly lower levels of frictional torque. It is also noteworthy that two of the three commonly used hip-joint systems as indicated above include a metallic femoral head articulating against a UHMWPE liner inside the acetabular cup. UHMWPE, being a polymeric material, is more susceptible to creep when heated than the commonly used metal alloys or ceramics due to its relatively lower melting point and is consequently more susceptible to wear than the alloys or ceramics.

It has also been found that metal prostheses are not completely inert in the body. Body fluids act upon the metals causing them to slowly corrode by an ionization process thereby releasing metal ions into the body. Metal ion release from the prosthesis is also related to the articulation and rate of wear of load bearing surfaces because, as may be expected, when a metallic femoral head, for instance, is articulated against UHMWPE, the passive oxide film which forms on the femoral head is constantly removed. The repassivation process constantly releases metal ions during this process. Furthermore, the presence of third-body wear (cement or bone debris) accelerates this process and micro fretted metal particles can increase friction. Consequently, the UHMWPE liner inside the acetabular cup, against which the femoral head articulates, is subjected to accelerated levels of creep, wear, and torque.

A number of attempts to correct these problems were the subject of much of the early work in this area. U.S. Pat. No. 4,145,764 to Suzuki taught a metal prosthesis plasma sprayed with a bonding agent which is in turn covered with a porous ceramic coating which would allow the in-growth of bone spicules into the pores. However, the Suzuki patent did not address the issue of friction or wear of orthopedic implant bearing surfaces but confined itself to the single issue of the biocompatibility of metal prostheses and did not address the issue of dimensional changes that occur when applying such a coating. U.S. Pat. No. 3,677,795 to Bokros is directed to the application of a carbide coating over a metallic prosthetic device. The method is said to produce a prosthetic device which has "excellent compatibility with body tissue and is non-thrombogenic". However, Bokros does not address the issues of friction, heating, creep and wear of orthopedic implant bearing surfaces, or changes induced in the mechanical properties of the underlying metal due to this high-temperature treatment.

The aforementioned failings of the prior art were addressed in part by Davidson in U.S. Pat. No. 5,037,438. In the '438 patent, Davidson teaches a zirconium or zirconium-containing metal alloy prosthesis coated via in-situ oxidation with a surface of blue-black or black oxidized zirconium. The oxidized zirconium coating provides the '438 invention prosthesis with a thin, dense, low friction, wear resistant, biocompatible surface ideally suited for use on articulating surfaces of joint prostheses wherein a surface or surfaces of the joint articulates, translates or rotates against mating joint surfaces. The oxidized zirconium coating of the '438 patent may therefore be usefully employed on the femoral heads or inside surfaces of acetabular cups of hip-joint implants or on the articulating surfaces of other types of prostheses, such as knee joints. Notably, the oxidized zirconium coating of the '438 patent was a specific type of oxidized zirconium. Oxidized zirconium presents itself in many forms, among them are white, beige, and blue-black. The white variety is particularly disfavored in the present application, as it tends to separate and break off of the substrate readily. Conventional oxidized zirconium surfaces formed, for example, by simple air oxidation will not be of the blue-black or black variety and will not possess the superior properties of the same which are recited in the '438 patent. The most important of these properties high hardness, low friction that results from the presence of the surface oxide.

These specific blue-black or black oxidized zirconium coatings were known in the art of mechanical bearings, having been originally taught by Watson in U.S. Pat. No. 2,987,352. Watson teaches a 700–1100° F. oxidation method to produced the specific blue-black or blue oxidized zirconium coating. The teachings of Watson '352 are incorporated by reference as though fully set forth. A later issuing patent to Haygarth (U.S. Pat. No. 4,671,824) teaches an alternative, salt-bath method to produce the desired coating. Haygarth '824 is also incorporated by reference as though fully set forth herein. The blue-black or black oxidized zirconium of the instant invention possessing the necessary properties is primarily monoclinic crystal structure. This has been characterized by Hunter et al.

The '438 patent did not contemplate and nowhere does it teach, the use of the oxidized zirconium surfaces directly contacting other surfaces of oxidized zirconium. To our knowledge, no such prosthetic devices or medical implants have been so fabricated. Initially, it was generally believed that the hardness of the two contacting surfaces were required to be of differing values. In this way, imperfections in the tolerances between the surfaces would disappear upon first contact, resulting in a long-lasting device relatively free of galling, fretting or other erosive phenomena. While efforts have been made to develop prosthetic devices having contacting surfaces of the same or very similar materials, success in overcoming the failings of the prior art devices without incurring other deficiencies has been limited.

The instant inventors have discovered that the unique properties of oxidized zirconium obviate the general need that one of the contacting surfaces to be of lesser hardness to extend the overall life of the device. The superior hardness, low friction, wear resistance, and biocompatibility characteristics of the blue-black or black oxidized zirconium is sufficient in itself to considerably slow and possibly prevent the degradative wear processes to which the prosthetic devices of the prior art have been subject.

The removal of surfaces of lesser hardness is expected to have other beneficial effect as well. This is particularly true in the case of the most commonly used articulating component, polyethylene; the most common type being ultra-high molecular weight polyethylene (UHMWPE). The original impetus for the inclusion of such surfaces was that they would act sacrificially; they would fail slowly and fail before the harder surface, allowing for an overall extension of the useful life of the device. Additionally, polyethylene was thought to absorb shock much better than harder surfaces, thereby mimicking real cartilage. While the advance in the art which was realized by the use of oxidized zirconium surfaces articulating against UHMWPE surfaces was a lessening of creep and cup loosening due to the heat generated between the surface of the metallic component and the UHMWPE, the problem was not completely eliminated. Thus, the instant invention represents another advancement in the art, namely, elimination of the creep problem associated with the prior art prostheses comprising polyethylene articulating surfaces.

Furthermore, it was eventually realized that UHMWPE had additional problems outside of eventual prosthesis failure. Osteolysis was observed in some prosthetic implant patients and was originally believed to be due to metal debris. As a result, prostheses of metal-on-polyethylene were replaced with ceramic-on-polyethylene systems such as alumina-on-polyethylene and zirconia-on-polyethylene. When it was suspected that polyethylene debris also contributed to the observed osteolysis, the first systems using contacting surfaces of the same material were introduced. The earliest of such devices were ceramic-on-ceramic. For example, Ceratec produced an alumina-on-alumina device while Norton-Desmarquest produced a zirconia-on-zirconia system. However, while ceramic has the advantage of low wear rates and low friction, it has its own disadvantages, the most important being its susceptibility to fracture. Most recently, metal-on-metal systems have been introduced. For example, Sulzer introduced a Cobalt/Chromium-on-Cobalt/Chromium device. Although metal-on-metal systems are expected to have low wear rates, questions remain regarding the metal ion release characteristics of such systems and the associated health risks to the patient.

The instant invention of prosthetic devices of oxidized zirconium-on-oxidized zirconium, in which both surfaces are of the blue-black or black variety, represents a special species of ceramic-on-ceramic devices, having the low wear rate and low friction advantages of ceramic systems, but without the concomitant high fracture risk. By eliminating the polyethylene, osteolysis risks and other issues associated with polyethylene wear debris are eliminated. Finally, the disadvantages associated with metal ion release of metal-on-metal designs are avoided as well. The unique properties of oxidized zirconium affords the ability to eliminate or minimize the disadvantages of the prior art systems without sacrificing the advantages of the same.

There exists a need for a metal alloy-based orthopedic implant having low friction, highly wear resistant load bearing surfaces which may be implanted for the lifetime of the recipient, low risk of brittle fracture, and low risk of metal-ion release. There also exists a need for a metal alloy-based orthopedic implant that is not prone to corrosion by the action of body fluids so that it is biocompatible and stable over the lifetime of the recipient. These needs must be met while maintaining a long service life, in order to minimize the frequency of and perhaps eliminate the need for surgical revisions for implant patients.

SUMMARY OF THE INVENTION

As used herein the specification, "a" or "an" may mean one or more. As used herein in the claim(s), when used in conjunction with the word "comprising", the words "a" or "an" may mean one or more than one. As used herein "another" may mean at least a second or more.

As used herein, the term "contacting surface" refers to any two surfaces of the prosthetic device or medical implant that contact one another in either a load bearing (articulating) or non-load bearing (non-articulating) manner.

The following discussion contains illustration and examples of preferred embodiments for practicing the present invention. However, they are not limiting examples. Other examples and methods are possible in practicing the present invention.

As used herein, "zirconium alloy" is defined as any metal alloy containing zirconium in any amount greater than zero. Thus, an alloy in which zirconium is a minor constituent is considered a "zirconium alloy" herein.

The invention provides a zirconium or zirconium-containing metal alloy prosthesis coated via in situ oxidation with blue-black or black oxidized zirconium. The oxidized zirconium coating provides the invention prosthesis with a thin, dense, low friction, wear resistant, biocompatible surface ideally suited for use on articulating surfaces of joint prostheses wherein a surface or surfaces of the joint articulates, translates, or rotates against mating joint surfaces which are also coated with oxidized zirconium. The oxidized zirconium coating may therefore be usefully employed on the femoral heads or inside surfaces of acetabular cups of hip-joint implants or on the articulating surfaces of other types of prostheses, such as knee joints.

In one embodiment of the present invention, a knee prosthesis for implantation in a patient, comprising a prosthesis body formed of zirconium or zirconium alloy comprising an implant portion for inserting into the body tissue of the patient. The prosthesis also has a bearing surface comprising at least one condyle on the prosthesis body, a tibial component formed of zirconium or zirconium alloy having a surface adapted to cooperate with the bearing surface and a thin coating of blue-black or black oxidized zirconium directly on the bearing surface of the condyle portion and on the cooperating surface of the tibial component. In a specific embodiment, at least one of the thin blue-black or black oxidized zirconium coating is from about 1 to about 20 microns thick. In another embodiment, it is from about 1 to about 5 microns thick.

Other embodiments have modifications designed to promote tissue in-growth or anchoring to native tissue or bone.

In one specific embodiment, the implant portion of the prosthesis body has, at least partially, an irregular surface structure adapted to accommodate tissue in-growth on a portion of the prosthesis body. In another such embodiment, the irregular surface structure is formed of zirconium or zirconium alloy beads attached to the outer surface of the prosthesis body, and at least a portion of the surface of the beads is oxidized to blue-black or black oxidized zirconium. In yet another embodiment, the irregular surface structure is formed of zirconium or zirconium alloy wire mesh connected to the outer surface of the prosthesis body, and at least a portion of the surface of the mesh is oxidized to blue-black or black oxidized zirconium.

Another embodiment comprises a hip prosthesis body for implantation into a femor which further comprises a head portion formed of zirconium or zirconium alloy, a bearing surface on the head portion of the prosthesis body, and an acetabular cup having an inner surface formed of zirconium or zirconium alloy. The inner surface of the acetabular cup is adapted to cooperate with the bearing surface on the head portion. A thin coating of blue-black or black oxidized zirconium exists directly on the bearing surface of the head portion and directly on the inner surface of said acetabular cup. In a specific embodiment of a hip prosthesis, at least one of the thin blue-black or black oxidized zirconium coating is from about 1 to about 5 microns thick.

Other embodiments have modifications designed to promote tissue in-growth or anchoring to native tissue or bone. In one specific embodiment, the prosthesis body has, at least partially, an irregular surface structure adapted to accommodate tissue in-growth on a portion of the prosthesis body. In another such embodiment, the irregular surface structure is formed of zirconium or zirconium alloy beads connected to the outer surface of the prosthesis body, wherein at least a portion of the surface of the beads is oxidized to blue-black or black oxidized zirconium. In yet another embodiment, the irregular surface structure is formed of zirconium or zirconium alloy wire mesh connected to the outer surface of the prosthesis body, wherein at least a portion of the surface of the mesh is oxidized to blue-black or black oxidized zirconium.

In another embodiment of the present invention, the prosthesis comprises a prosthesis body of zirconium or zirconium alloy. The body comprising an implant portion for insertion into the body tissue of the patient, and a bearing surface on the prosthesis body. The bearing surface is sized and shaped to engage or cooperate with a second bearing surface on another prosthesis portion, the second bearing surface also is formed of zirconium or zirconium alloy. Additionally, coating of blue-black or black oxidized zirconium from about 1 to about 5 microns in thickness on the bearing surface of the prosthesis and on said second bearing surface of said another prosthesis portion. In a specific embodiment, the prosthesis body is a hip joint having a head portion as a bearing surface and another prosthesis portion is an acetabular cup. The head portion is adapted to cooperate with the inner surface of the acetabular cup, and the inner surface of the acetabular cup also acts as the second bearing surface.

In alternative embodiments, the prosthesis body may be a knee joint and the bearing surface of the prosthesis body comprises at least one condyle, and another prosthesis portion comprises a tibial component, with the condyle(s) being adapted to cooperate with the tibial component. Alternatively, the prosthesis body has an irregular surface structure adapted to accommodate tissue in-growth on at least a portion of the prosthesis body. In another embodiment, the irregular surface structure is formed of zirconium or zirconium alloy beads connected to the outer surface of the prosthesis body, and at least a portion of the surface of the beads is oxidized to blue-black or black oxidized zirconium. In yet another embodiment, the irregular surface structure is formed of zirconium or zirconium alloy wire mesh connected to the outer surface of the prosthesis body, and at least a portion of the surface of the mesh is oxidized to blue-black or black oxidized zirconium.

In another embodiment, a prosthesis for implantation has a prosthesis body formed of zirconium or zirconium alloy comprising an implant portion for inserting into the body tissue of the patient and a bearing surface on the prosthesis body. A counter-bearing surface formed of zirconium or zirconium alloy and adapted to cooperate with the bearing surface and a thin coating of blue-black or black oxidized zirconium directly on the bearing surface and on the counter-bearing surface are also present. Preferably, the prosthesis has at least one of the thin blue-black or black oxidized zirconium coatings of a thickness of about 1 to about 20 microns. In another embodiment, it is from about 1 to about 5 microns thick.

In an alternative embodiment, the implant portion of the prosthesis body has an irregular surface structure adapted to accommodate tissue in-growth on a portion of the prosthesis body. Alternatively, the irregular surface structure is formed of zirconium or zirconium alloy beads attached to the outer surface of the prosthesis body, and at least a portion of the surface of the beads is oxidized to blue-black or black oxidized zirconium. In another embodiment, the irregular surface structure is formed of zirconium or zirconium alloy wire mesh connected to the outer surface of the prosthesis body, and at least a portion of the surface of the mesh is oxidized to blue-black or black oxidized zirconium. In another embodiment, there is a non-articulating medical implants having more than one surface of oxidized zirconium in which at least two such surfaces of oxidized zirconium contact one another. Specific embodiments of such non-articulating implants include, but are not limited to, bone plates, bone screws, skull plates, mandibular implants, dental implants, internal fixators, external fixators, spatial frames, pins, nail, wires, and staples

DESCRIPTION OF THE DRAWINGS

FIG. 1 is a schematic diagram depicting a hip joint prosthesis in position.

FIG. 2 is a schematic diagram showing a typical hip joint prosthesis.

FIG. 3 is a schematic diagram of a knee joint prosthesis in place.

FIG. 4 is a schematic diagram of the parts of a typical knee joint.

DETAILED DESCRIPTION OF THE INVENTION

The present invention provides low friction, wear resistant coatings on the articulating surfaces of prosthetic devices. Specifically, the invention provides for a prosthetic device in which the contacting surfaces are comprised of blue-black or black oxidized zirconium. Oxidized zirconium presents itself in many forms, among them are white, beige, and blue-black. The white variety is particularly disfavored in the present application, as it tends to separate and break off of the substrate readily. Conventional oxidized zirconium surfaces formed, for example, by simple air oxidation will not be of the blue-black or black variety. The blue-black or black oxidized zirconium of the instant invention possessing the necessary properties is primarily monoclinic crystal structure and may include tetragonal zirconia. Its microstructure has been characterized by Hunter et. al. The specific blue-black or black oxidized zirconium coatings used herein were known in the art of mechanical bearings, having been originally taught by Watson in U.S. Pat. No. 2,987,352. Davidson, in U.S. Pat. No. 5,037,428 first taught the application of this form of oxidized zirconium to prosthetic devices but did not teach or suggest their use in directly contacting other oxidized zirconium surfaces. Illustrative examples of the use of blue-black or black oxidized zirconium on prosthetic devices are shown in the schematic diagrams, FIGS. 1–4.

A typical hip joint assembly is shown in situ in FIG. 1 and FIG. 2. The hip joint stem 2 fits into the femur while the femoral head 6 of the prosthesis fits into and articulates against the inner lining 8 of an acetabular cup 10 which in turn is affixed to the pelvis as shown in FIG. 1. A porous metal bead or wire mesh coating 12 may be incorporated to allow stabilization of the implant by in-growth of surrounding tissue into the porous coating. Similarly, such a coating can also be applied to the acetabular component. The femoral head 6 may be an integral part of the hip joint stem 2 or may be a separate component mounted upon a conical taper at the end of the neck 4 of the hip joint prosthesis. This allows the fabrication of a prosthesis having a metallic stem and neck but a femoral head of a different material. This method of construction is often desirable because the use of composite materials allows for the localized optimization of a variety of parameters such as weight, strength and wear resistance. Regardless of the materials, however, the femoral head articulates against the inner surface of the acetabular cup thereby causing wear and, in the long term, this may necessitate prosthesis replacement. This is especially the case where the femoral head is of metal and the acetabular cup is lined with an organic polymer or composite thereof. While these polymeric surfaces provide good, relatively low friction surfaces and are biocompatible, they are, as explained above, subject to wear and accelerated creep due to the frictional heat and torque to which they are subjected during ordinary use. In the present invention, the inner lining 8 and the femoral head 6 are coated with a surface of blue-black or black oxidized zirconium. Preferably, the surface coatings are 1–20 $\mu$m thick, but may be outside this range. They may alternatively be from about 1–5 $\mu$m thick. The wire mesh or metal bead surface 12 may be at least partially coated with a surface of blue-black or black oxidized zirconium to promote in-growth of tissue or bone into the device, thereby stabilizing its position.

A typical knee joint prosthesis is shown in situ in FIG. 3 and FIG. 4. The knee joint includes a femoral component 20 and a tibial component 30. The femoral component includes condyles 22 which provide the articulating surface of the femoral component and pegs 24 for affixing the femoral component to the femur. The tibial component 30 includes a tibial base 32 with a peg 34 for mounting the tibial base onto the tibia. A tibial platform 36 is mounted atop the tibial base 32 and is supplied with grooves 38 similar to the shape of the condyles 22. The bottom surfaces of the condyles 26 contact the tibial platform's grooves 38 so that the condyles articulate within these grooves against the tibial platform. Both the condyles 22 and the grooves 38 on the tibial platform 36 are coated with a surface of blue-black or black oxidized zirconium. Part or all of the remainder of the femoral component 20 and a tibial component 30 may have a surface coating of blue-black or black oxidized zirconium. Preferably, the surface coatings are 1–20 μm thick, but may be outside this range. They may alternatively be from about 1–5 μm thick. As in the case of the hip joint, porous bead or wire mesh coatings can also be applied to either the tibial or femoral components of the knee or both. These porous bead or wire mesh coatings of the knee prosthesis may also be at least partially coated with a surface of blue-black or black oxidized zirconium to promote in-growth of tissue or bone into the device, thereby stabilizing its position.

The invention provides oxidized zirconium coated orthopedic implants or prostheses fabricated of zirconium or zirconium containing metal alloys or a thin coating of zirconium or zirconium alloy on conventional orthopedic implant materials. In order to form continuous and useful oxidized zirconium coatings over the desired surface of the metal alloy prosthesis substrate, the metal alloy preferably should contain from about 80 to about 100 wt. % zirconium, and more preferably from about 95 to about 100 wt. %. However, much lesser amounts of zirconium may still produce acceptable product. For example, a titanium alloy having 13% zirconium, 13% niobium (Ti-13-13) has been shown to yield an acceptable oxidized zirconium surface. Lesser amounts of zirconium are expected to also yield acceptable surface coating. X-ray Photoelectron Spectroscopy results shown in Tables 1 and 2 for the Ti-13-13 alloy, reveal the atomic concentrations (normalized to 100%) of the individual elements and the various oxides. Thus, because acceptable product is obtained where zirconium and its oxides are present as minor constituents, a wider range of alloys, including those in which zirconium is a minor component are useful in the invention.

TABLE 1

Atomic Concentration of the Elements in the Near Surface of Surface Oxidized As Determined by X-Ray Photoelectron Spectroscopy (XPS) Analysis.

| Depth, Å | O | Ti | N | Nb | Zr | C |
|---|---|---|---|---|---|---|
| Surface | 36.2 | 7.4 | 1.0 | 0.2 | 0.1 | 55.1 |
| 50 | 65.7 | 29.7 | 0.0 | 0.6 | 0.6 | 3.4 |
| 200 | 62.1 | 32.7 | 0.0 | 1.5 | 1.7 | 2.0 |
| 1,000 | 59.8 | 27.3 | 0.0 | 5.6 | 5.5 | 1.9 |
| 2,000 | 58.4 | 29.9 | 0.0 | 5.6 | 5.0 | 1.1 |
| 5,000 | 55.4 | 32.3 | 0.0 | 6.0 | 5.3 | 1.0 |
| 10,000 | 37.2 | 43.5 | 0.0 | 8.3 | 6.3 | 4.6 |
| 15,000 | 23.5 | 51.9 | 0.0 | 10.0 | 7.3 | 7.2 |
| 20,000 | 14.0 | 59.7 | 0.7 | 13.1 | 8.4 | 4.1 |

TABLE 2

Concentrations of Ti, Nb and Zr Oxides Contained in the Mixed Oxide Layer for Surface Oxidized Ti-13-13.

| Depth, Å | $TiO_2$ | $TiO_x$ | TiO | $Nb_2O_5$ | $NbO_x$ | $ZrO_2$ | $ZrO_x$ |
|---|---|---|---|---|---|---|---|
| 50 | 28.7 | 67.3 | 0.0 | 2.0 | 0.0 | 2.0 | 0.0 |
| 200 | 23.6 | 51.1 | 16.4 | 0.0 | 4.0 | 4.4 | 0.6 |
| 1,000 | 14.6 | 36.7 | 22.1 | 0.0 | 15.0 | 12.0 | 2.0 |
| 2,000 | 13.8 | 32.1 | 18.3 | 0.0 | 14.0 | 10.3 | 1.7 |
| 5,000 | 13.6 | 36.6 | 22.9 | 0.0 | 14.0 | 9.6 | 2.4 |

Oxygen, niobium, and titanium are common alloying elements in the alloy with oftentimes the presence of hafnium. While such zirconium containing alloys may be custom formulated by conventional methods known in the art of metallurgy, a number of suitable alloys are commercially available. Illustrative examples of these commercial alloys include among others Zircadyne 705, Zircadyne 702, and Zircalloy.

The base zirconium containing metal alloys are cast or machined by conventional methods to the shape and size desired to obtain a prosthesis substrate. The substrate is then subjected to process conditions which cause the natural (in situ) formation of a tightly adhered, diffusion-bonded coating of oxidized zirconium on its surface. The process conditions include, for instance, air, steam, or water oxidation or oxidation in a salt bath. These processes ideally provide a thin, hard, dense, blue-black or black, low-friction wear-resistant oxidized zirconium film or coating of thickness typically on the order of several microns ($10^{-6}$ meters) on the surface of the prosthesis substrate. Below this coating, diffused oxygen from the oxidation process increases the hardness and strength of the underlying substrate metal.

Representative methods for the formation of the surface coating of blue-black or black oxidized zirconium have been described previously in U.S. Pat. No. 5,037,428 to Davidson, which is incorporated by reference as though fully set forth herein. A coating thickness of 1 to 5 microns is preferred. Conditions useful for the fabrication of surfaces of varying thickness are described in U.S. Pat. No. 5,037,428. Methods for controlling the uniformity of the oxidized zirconium coating are described in the commonly-assigned copending application Ser. No. 09/381,217, which is incorporated by reference as though fully set forth herein.

These diffusion-bonded, low friction, highly wear resistant oxidized zirconium coatings are applied to the contacting surfaces of orthopedic implants subject to conditions of wear. Such surfaces include the articulating surfaces of knee joints, elbows and hip joints. As mentioned before, in the case of hip joints, the femoral head and stem are typically fabricated of metal alloys while the acetabular cup may be fabricated from ceramics. The only requirement is that the contacting surface of the device must be of zirconium or zirconium alloy such that upon surface oxidation under the appropriate conditions, measurable surface concentrations of oxidized zirconium are formed.

The prostheses of the instant invention exhibit advantages in a variety of applications. Hip prostheses are a comparatively simple mechanical system, consisting of a spherical head, a spherical cavity and a simple taper in the stem. The range of mechanical loading states in this configuration is comparatively small. Thus, one can design the head so that a brittle material such as ceramic may be used while maintaining a relatively low brittle fracture risk. In contrast, a knee joint is a less-conforming joint having a greater range of mechanical loading states. The knee joint has a higher risk of experiencing "point loading"; i.e., highly localized stress levels. Thus, in knee applications, a brittle material on another brittle material such as conventional ceramic-on-ceramic has a higher likelihood of fracture. For this reason, it was found to be particularly important to design such prostheses as "hard-on-soft" systems, such as ceramic-on-polyethylene. While ceramic-on-ceramic prostheses have the advantages of low friction and low wear rates, they suffer from the disadvantage of a high brittle fracture risk. Thus, such ceramic-on-ceramic systems (and indeed all "hard-on-hard" systems, to some degree) are problematic in both knee and hip prostheses, but are particularly ill-suited for knee prostheses. Although it is a ceramic-on-ceramic system, the oxidized zirconium of the instant invention has the general advantages of the same; i.e., low friction and high wear resistance, but it does not suffer from the major disadvantage of such systems of high brittle fracture risk. Thus, the instant invention has general application across different prostheses, allowing one to realize the advantages of ceramic-onceramic while avoiding its disadvantages. The oxidized zirconium-on-oxidized zirconium prostheses of the present invention have general applicability in the both the prostheses used in "hard-on-hard" applications and in those of traditional "hard-on-soft" applications. It is suited for use in a variety of prosthetic devices that experience a wide range of mechanical loading states.

The usefulness of oxidized zirconium coated prosthesis is not limited to load bearing prostheses, especially joints, where a high rate of wear may be encountered. Because the oxidized zirconium coating is firmly bonded to the zirconium alloy prosthesis substrate, it provides a barrier between the body fluids and the zirconium alloy metal thereby preventing the corrosion of the alloy by the process of ionization and its associated metal ion release. Additionally, oxygen diffusion into the metal substrate during oxidation also increases the strength of the metal. Consequently, an oxidized zirconium coated prosthesis may be expected to have a greater useful service life.

Zirconium or zirconium alloy can also be used to provide a porous bead or wire mesh surface to which surrounding bone or other tissue may integrate to stabilize the oxidized zirconium-on-oxidized zirconium prosthesis. These porous coatings can be treated simultaneously by the oxidation treatment in a manner similar to the oxidation of the base prosthesis for the elimination or reduction of metal ion release. Furthermore, zirconium or zirconium alloy can also be used as a surface layer applied over conventional implant materials prior to in situ oxidation and formation of the oxidized zirconium coating.

The oxidized zirconium-on-oxidized zirconium of the present invention is useful in non-articulating implant applications as well. Shoulder, spine and other prosthetic applications where fretting is a primary concern will benefit from the unique properties of oxidized zirconium. For example, an oxidized zirconium bone screw on an oxidized zirconium bone plate will benefit from all advantages discussed above.

Although the invention has been described with reference to its preferred embodiments, those of ordinary skill in the art may, upon reading this disclosure, appreciate changes and modifications which may be made and which do not depart from the scope and spirit of the invention as described above or claimed hereafter.

References

All patents and publications mentioned in the specification are indicative of the level of those skilled in the art to which the invention pertains. All patents and publications are herein incorporated by reference to the same extent as if each individual publication was specifically and individually indicated to be incorporated by reference.

| U.S. Pat. No. 5,037,438 | August 1991 | Davidson |
| U.S. Pat. No. 4,145,746 | March 1979 | Suzuki et al. |
| U.S. Pat. No. 3,677,795 | July 1972 | Bokros et al. |
| U.S. Pat. No. 2,987,352 | February 1958 | Watson |
| U.S. Pat. No. 4,671,824 | June 1987 | Haygarth |
| U.S. application Ser. No. 09/381,217 | filed November 1999 | Hunter et al. |

Hunter, G. et al., Mat. Res. Soc. Symp. Proc., 1999, 550, 337.

What is claimed is:

1. A prosthesis for implantation in a patient, comprising:
   (a) a prosthesis body formed of zirconium or zirconium alloy comprising an implant portion for inserting into the body tissue of the patient;
   (b) a bearing surface comprising at least one condyle on the prosthesis body;
   (c) a tibial component formed of zirconium or zirconium alloy having a surface adapted to cooperate with the bearing surface; and,
   (d) a thin coating of blue-black or black oxidized zirconium directly on the bearing surface of the condyle portion and on the cooperating surface of the tibial component.

2. The prosthesis of claim 1 wherein at least one of said thin blue-black or black oxidized zirconium coating is from about 1 to about 20 microns thick.

3. The prosthesis of claim 1 wherein at least one of said thin blue-black or black oxidized zirconium coating is from about 1 to about 5 microns thick.

4. The prosthesis of claim 1 wherein the implant portion of the prosthesis body further comprises an irregular surface structure adapted to accommodate tissue in-growth on a portion of the prosthesis body.

5. The prosthesis of claim 4 wherein the irregular surface structure is formed of zirconium or zirconium alloy beads attached to the outer surface of the prosthesis body, wherein at least a portion of the surface of the beads is oxidized to blue-black or black oxidized zirconium.

6. The prosthesis of claim 4 wherein the irregular surface structure is formed of zirconium or zirconium alloy wire mesh connected to the outer surface of the prosthesis body, wherein at least a portion of the surface of the mesh is oxidized to blue-black or black oxidized zirconium.

7. A prosthesis for implantation in a patient, comprising:
   (a) a hip prosthesis body for implantation into a femor comprising a head portion formed of zirconium or zirconium alloy;
   (b) a bearing surface on the head portion of the prosthesis body;
   (c) an acetabular cup having an inner surface formed of zirconium or zirconium alloy, said inner surface being adapted to cooperate with the bearing surface on the head portion; and,
   (d) a thin coating of blue-black or black oxidized zirconium directly on the bearing surface of the head portion and directly on the inner surface of said acetabular cup.

8. The prosthesis of claim 7 wherein at least one of said thin blue-black or black oxidized zirconium coating is from about 1 to about 20 microns thick.

9. The prosthesis of claim 7 wherein at least one of said thin blue-black or black oxidized zirconium coating is from about 1 to about 5 microns thick.

10. The prosthesis of claim 7 wherein the prosthesis body further comprises an irregular surface structure adapted to accommodate tissue in-growth on a portion of the prosthesis body.

11. The prosthesis of claim 10 wherein the irregular surface structure is formed of zirconium or zirconium alloy wire mesh connected to the outer surface of the prosthesis body, wherein at least a portion of the surface of the mesh is oxidized to blue-black or black oxidized zirconium.

12. The prosthesis of claim 10 wherein the irregular surface structure is formed of zirconium or zirconium alloy beads connected to the outer surface of the prosthesis body, wherein at least a portion of the surface of the beads is oxidized to blue-black or black oxidized zirconium.

13. A prosthesis for implantation in a patient, comprising:
   (a) a prosthesis body formed of zirconium or zirconium alloy comprising an implant portion for insertion into the body tissue of the patient;

(b) a bearing surface on the prosthesis body, the bearing surface being sized and shaped to engage or cooperate with a second bearing surface on another prosthesis portion, said second bearing surface being formed of zirconium or zirconium alloy; and, (c) a coating of blue-black or black oxidized zirconium from about 1 to about 5 microns in thickness on the bearing surface of the prosthesis and on said second bearing surface of said another prosthesis portion.

14. The prosthesis of claim 13 wherein the prosthesis body is a hip joint having a head portion as a bearing surface and wherein said another prosthesis portion is an acetabular cup, said head portion being adapted to cooperate with the inner surface of the acetabular cup, wherein said inner surface of said acetabular cup is also said second bearing surface.

15. The prosthesis of claim 13 wherein the prosthesis body is a knee joint and the bearing surface of the prosthesis body comprises at least one condyle, and wherein said another prosthesis portion comprises a tibial component, said at least one condyle being adapted to cooperate with said tibial component.

16. The prosthesis of claim 13 wherein the prosthesis body further comprises an irregular surface structure adapted to accommodate tissue in-growth on at least a portion of the prosthesis body.

17. The prosthesis of claim 16 wherein the irregular surface structure is formed of zirconium or zirconium alloy beads connected to the outer surface of the prosthesis body, wherein at least a portion of the surface of the beads is oxidized to blue-black or black oxidized zirconium.

18. The prosthesis of claim 16 wherein the irregular surface structure is formed of zirconium or zirconium alloy wire mesh connected to the outer surface of the prosthesis body, wherein at least a portion of the surface of the mesh is oxidized to blue-black or black oxidized zirconium.

19. A prosthesis for implantation in a patient, comprising:

(a) a prosthesis body formed of zirconium or zirconium alloy comprising an implant portion for inserting into the body tissue of the patient;

(b) a bearing surface on the prosthesis body;

(c) a counter-bearing surface formed of zirconium or zirconium alloy and adapted to cooperate with the bearing surface; and, (d) a thin coating of blue-black or black oxidized zirconium directly on the bearing surface and on the counter-bearing surface.

20. The prosthesis of claim 19 wherein at least one of said thin blue-black or black oxidized zirconium coating is from about 1 to about 20 microns thick.

21. The prosthesis of claim 19 wherein at least one of said thin blue-black or black oxidized zirconium coating is from about 1 to about 5 microns thick.

22. The prosthesis of claim 19 wherein the implant portion of the prosthesis body further comprises an irregular surface structure adapted to accommodate tissue in-growth on a portion of the prosthesis body.

23. The prosthesis of claim 22 wherein the irregular surface structure is formed of zirconium or zirconium alloy beads attached to the outer surface of the prosthesis body, wherein at least a portion of the surface of the beads is oxidized to blue-black or black oxidized zirconium.

24. The prosthesis of claim 22 wherein the irregular surface structure is formed of zirconium or zirconium alloy wire mesh connected to the outer surface of the prosthesis body, wherein at least a portion of the surface of the mesh is oxidized to blue-black or black oxidized zirconium.

25. The prosthesis of claim 19 wherein said prosthesis is a spinal prosthesis.

26. The prosthesis of claim 19 wherein said spinal prosthesis is a spinal disc prosthesis.

27. A non-articulating medical implant comprising more than one surface of oxidized zirconium wherein at least one said surface of oxidized zirconium directly contacts another said surface of oxidized zirconium.

28. The non-articulating medical implant of claim 27 selected from the group consisting of bone plates, bone screws, skull plates, mandibular implants, dental implants, internal fixators, external fixators, spatial frames, pins, nails, wires, and staples.

* * * * *